(12) United States Patent  (10) Patent No.: US 8,399,245 B2
Leuthaeuser et al.  (45) Date of Patent: Mar. 19, 2013

(54) ROTATION SYSTEM FOR CELL GROWTH CHAMBER OF A CELL EXPANSION SYSTEM AND METHOD OF USE THEREFOR

(75) Inventors: Paul M. Leuthaeuser, Louisville, CO (US); Jon A. Dodd, Littleton, CO (US); Thomas G. DiLorenzo, Arvada, CO (US)

(73) Assignee: Terumo BCT, Inc., Lakewood, CO (US)

( * ) Notice: Subject to any disclaimer, the term of this patent is extended or adjusted under 35 U.S.C. 154(b) by 455 days.

(21) Appl. No.: 12/703,041

(22) Filed: Feb. 9, 2010

(65) Prior Publication Data

US 2010/0210016 A1 Aug. 19, 2010

Related U.S. Application Data

(60) Provisional application No. 61/159,690, filed on Mar. 12, 2009, provisional application No. 61/153,583, filed on Feb. 18, 2009.

(51) Int. Cl.
*C12M 1/10* (2006.01)
*C12M 1/00* (2006.01)
*C12M 3/00* (2006.01)

(52) U.S. Cl. .................. 435/298.2; 435/394; 435/298.1; 435/289.1; 366/209; 366/217

(58) Field of Classification Search ............... 435/289.1, 435/298.1, 298.2, 394; 366/209, 217
See application file for complete search history.

(56) References Cited

U.S. PATENT DOCUMENTS

| | | | |
|---|---|---|---|
| 4,824,787 A | 4/1989 | Serkes et al. | |
| 4,918,019 A | 4/1990 | Guinn | |
| 5,151,368 A * | 9/1992 | Brimhall et al. | 435/286.7 |
| 5,501,522 A * | 3/1996 | Tung | 366/219 |
| 5,688,687 A | 11/1997 | Palsson et al. | |
| 5,882,918 A | 3/1999 | Goffe | |
| 5,985,653 A | 11/1999 | Armstrong et al. | |
| 6,048,721 A | 4/2000 | Armstrong et al. | |
| 6,096,532 A | 8/2000 | Armstrong et al. | |
| 6,238,908 B1 | 5/2001 | Armstrong et al. | |
| 6,566,126 B2 | 5/2003 | Cadwell | |

(Continued)

FOREIGN PATENT DOCUMENTS

GB 1277544 6/1972
WO 02/28996 4/2002

(Continued)

OTHER PUBLICATIONS

International Search Report and Written Opinion issued Jun. 15, 2010 in Application No. PCT/US2010/023750.

(Continued)

*Primary Examiner* — Nathan Bowers
(74) *Attorney, Agent, or Firm* — René A. Pereyra; John R. Merkling; Elizabeth J. Reagan

(57) ABSTRACT

A system and method for rotating a cell growth chamber of a cell expansion system includes a rotatable member for engaging a chamber coupling attached to the cell growth chamber. The rotatable member includes an independently operable mechanism for engaging a rotatable fitting associated with the chamber coupling. In at least one embodiment, the chamber coupling is selectively rotatable by turning the rotatable member, thereby rotating the cell growth chamber around a first axis. The cell growth chamber is also selectively rotatable around a second axis by turning the rotatable fitting associated with the chamber coupling. Other novel aspects include a way of attaching the cell growth chamber to the shaft assembly, and a new tube routing clip.

10 Claims, 18 Drawing Sheets

U.S. PATENT DOCUMENTS

| | | |
|---|---|---|
| 6,642,019 B1 | 11/2003 | Anderson et al. |
| 6,979,308 B1 | 12/2005 | MacDonald et al. |
| 7,112,441 B2 | 9/2006 | Uemura et al. |
| 7,198,940 B2 | 4/2007 | Vellinger et al. |
| 2004/0011747 A1* | 1/2004 | Dolecek .................. 210/787 |
| 2006/0019388 A1 | 1/2006 | Hutmacher et al. |
| 2008/0213894 A1 | 9/2008 | Antwiler |
| 2008/0220523 A1 | 9/2008 | Antwiler |

FOREIGN PATENT DOCUMENTS

| | | |
|---|---|---|
| WO | 02/087491 | 11/2002 |
| WO | 03/092573 | 11/2003 |
| WO | 2006/026835 | 3/2006 |
| WO | 2009/034186 | 3/2009 |

OTHER PUBLICATIONS

Biovest International, "AutovaxID-C—A breakthrough technology in the production of biologics for the Biotechnology industry", http://www.biovest.com/AutovaxIDInstruments.htm, Jan. 17, 2007, 2 pages.

dBusinessNews, "Biovest's AutovaxID(TM) Cleared for Commercial Sale", http://www.seattle.dbusinessnews.com/shownews.php?news.id=75401&type_news=past, Jan. 19, 2007, 2 pages.

Terumo, "Home\Products\Sterile Tubing Welders\TSCD", from Terumotransfusion.com, Apr. 7, 2008, 1 page.

Whiteford et al., "Interest in Hollow-Fiber Perfusion Bioreactors is Growing", BioProcess International, Oct. 2009, pp. 54-63.

* cited by examiner

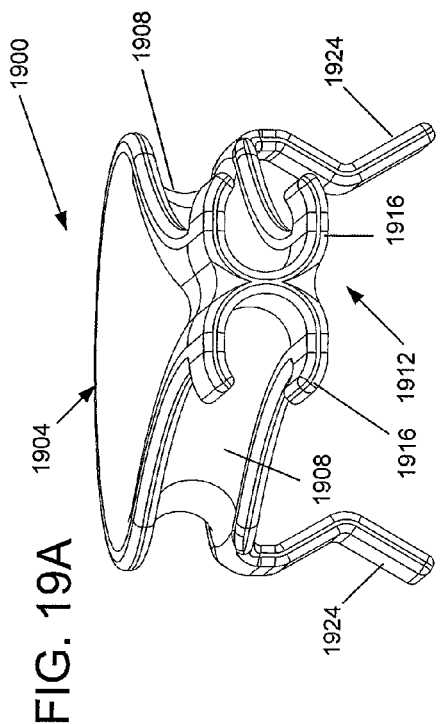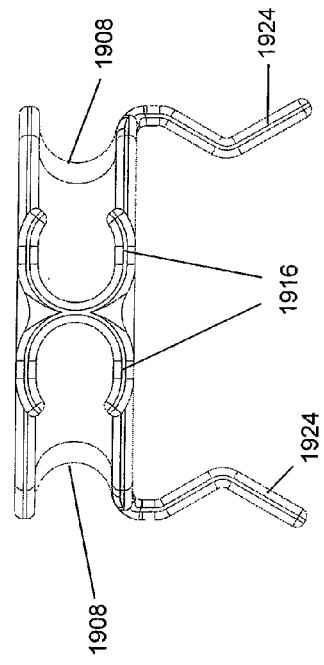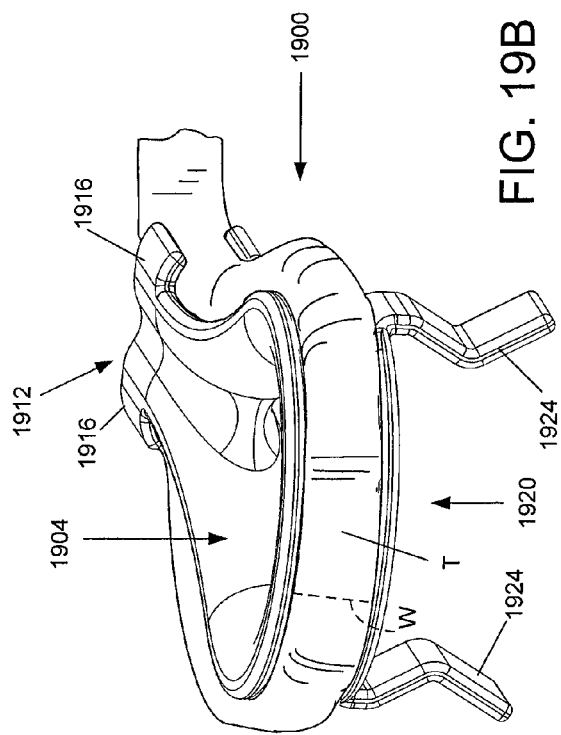

ROTATION SYSTEM FOR CELL GROWTH CHAMBER OF A CELL EXPANSION SYSTEM AND METHOD OF USE THEREFOR

CROSS REFERENCE TO RELATED APPLICATIONS

The present application claims the benefit of U.S. Provisional Patent Application No. 61/159,690 filed on Mar. 12, 2009, and U.S. Provisional Patent Application No. 61/153,583 filed on Feb. 18, 2009, both of which are expressly incorporated herein by reference.

The present application cross references, but does not claim priority to U.S. patent application Ser. No. 12/042,798 (corresponding to U.S. Pat. App. Pub. No. 2008/0220523) filed on Mar. 5, 2008, the content of which is incorporated herein by reference in its entirety.

FIELD

The present disclosure relates to a system and method for rotating a cell growth chamber of a cell expansion system (CES) that is used to grow cells.

BACKGROUND

CESs are used to expand and differentiate cells. Cell expansion systems are known in the art. For example, U.S. Pat. Nos. 5,162,225 and 6,001,585 generally describe cell expansion systems designed for cell expansion.

The potential use of stem cells in a variety of treatments and therapies has achieved particular attention. Cell expansion systems can be used to grow stem cells, as well as other types of cells, such as bone marrow cells. Stem cells which are expanded from donor cells can be used to repair or replace damaged or defective tissues and have broad clinical applications for a wide range of diseases. Recent advances in the regenerative medicine field demonstrates that stem cells have properties such as proliferation and self-renewal capacity, maintenance of the unspecialized state, and the ability to differentiate into specialized cells under particular conditions.

Cell expansion systems include one or more compartments for growing the cells, such as a cell growth chamber (also referred to herein as the "bioreactor"). However, a CES with a stationary cell growth chamber may limit the production of cells as compared to a system that provides some ability to adjust the position of the cell growth chamber. By way of example, adjusting the orientation of the cell growth chamber during a priming sequence allows the air or gas bubbles or pockets residing within the cell growth chamber to be driven from the cell growth chamber as the cell growth chamber is primed with a priming fluid. In addition, it is also advantageous to adjust the orientation of the cell growth chamber while cells are growing within the cell growth chamber to mitigate problems associated with cells settling within the cell growth chamber under the influence of gravity.

Accordingly, there is a need for a system of adjusting the position of a cell growth chamber associated with a cell expansion system. The present disclosure addresses this and other needs.

SUMMARY

It is to be understood that the present invention includes a variety of different versions or embodiments, and this Summary is not meant to be limiting or all-inclusive. This Summary provides some general descriptions of some of the embodiments, but may also include some more specific descriptions of other embodiments.

One or more embodiments are generally directed to a system for rotating a cell growth chamber of a cell expansion system. More particularly, as set forth below, at least one embodiment comprises a system for rotating a cell growth chamber about a first rotational axis and also about a second rotational axis. Accordingly, an apparatus for rotating a cell growth chamber of a cell expansion system is provided, the cell growth chamber including a longitudinal axis, the apparatus comprising:

a shaft assembly including:
an outer shaft member;
an inner shaft member wherein at least a portion of the inner shaft member is located radially to the interior of the outer shaft member, wherein the outer shaft member and the inner shaft member are substantially coaxial and share a shaft rotation axis, the inner shaft member including a beveled pinion at a distal end of the inner shaft member, wherein the beveled pinion is translatable longitudinally along the shaft rotation axis, the beveled pinion including a beveled surface;
a first motor for rotating the outer shaft member; and
a second motor for rotating the inner shaft member;
a chamber coupling connected to the cell growth chamber, the chamber coupling including a shaft fitting for detachably engaging the outer shaft member, the chamber coupling including a roll collar located around at least a portion of the cell growth chamber, the roll collar including a sloped surface for engaging the beveled pinion;
wherein when the first motor rotates the outer shaft member the cell growth chamber rotates around the shaft rotation axis, and wherein when the second motor rotates the inner shaft member the cell growth chamber rotates around the longitudinal axis of the cell growth chamber.

In at least one embodiment the beveled pinion comprises a substantially frusto-conical-shaped exterior including the beveled surface for frictionally contacting the sloped surface of the roll collar. In at least one embodiment the beveled pinion contacts the sloped surface along a contact line, the contact line oriented at an oblique angle relative to the longitudinal axis of the cell growth chamber. In at least one embodiment the beveled pinion contacts the sloped surface along a contact line, wherein a bevel angle θ between the contact line and the shaft rotation axis is substantially an inverse tangent value of a ratio of the beveled pinion diameter to the roll collar diameter. In at least one embodiment the inner shaft member includes a beveled pinion fitting, the beveled pinion fitting including a slotted sleeve that slidably engages a portion of the inner shaft member. In at least one embodiment, a pin transfers torque between the inner shaft member and the beveled pinion fitting. Embodiments may further include a biasing member for maintaining the beveled pinion in a distally biased position. In at least one embodiment at least one of the shaft fitting and the outer shaft member comprise an alignment guide for properly orienting the chamber coupling for attachment to the outer shaft member. In at least one embodiment, the shaft fitting comprises at least one spring member having a beveled distal end and a shoulder, wherein the beveled distal end deflects upon insertion into the outer shaft member, and wherein once the shoulder clears a front edge of a receptacle of the outer shaft member, the spring member moves radially outward and causes the shoulder to engage the front edge of the receptacle to detachably engage the chamber coupling and the cell growth chamber to the shaft assembly.

In at least one embodiment a tubing spool is connected to the chamber coupling, and a tube routing clip is detachably attached to the tubing spool, the tube routing clip including a substantially teardrop-shaped tube routing channel for holding a section of tubing.

One or more embodiments may include one or more ways of performing a particular function. Accordingly, an apparatus for rotating a cell growth chamber of a cell expansion system is provided, the cell growth chamber including a longitudinal axis, the apparatus comprising:

means for rolling the cell growth chamber around at least one of:
(a) the longitudinal axis of the cell growth chamber; and
(b) an axis substantially parallel to the longitudinal axis of the cell growth chamber; and means for pitching the cell growth chamber such that the longitudinal axis of the cell growth chamber rotates.

In at least one embodiment, the means for rolling and the means for pitching comprise independently rotatable coaxial shaft members. In at least one embodiment the means for rolling comprises a beveled pinion that contacts a sloped surface of a roll collar attached to the cell growth chamber, and wherein when the beveled pinion rotates around a rotational axis of the beveled pinion the roll collar rotates the cell growth chamber around the longitudinal axis of the cell growth chamber. In at least one embodiment the means for pitching comprises an outer shaft member, the means for rolling comprises an inner shaft member, and at least a portion of the inner shaft member is located radially to the interior of the outer shaft member to provide the independently rotatable coaxial shaft members. In at least one embodiment, a means for coupling the cell growth chamber to the outer shaft member is provided. In at least one embodiment, the means for coupling includes a shaft fitting, the shaft fitting comprising at least one spring member having a beveled distal end and a shoulder, wherein the beveled distal end deflects upon insertion into the outer shaft member, and wherein once the shoulder clears a front edge of a receptacle of the outer shaft member, the spring member moves radially outward and causes the shoulder to engage the front edge of the receptacle to detachably interconnect the cell growth chamber to the outer shaft member.

In at least one embodiment the means for rolling comprises a beveled pinion that contacts a sloped surface of a roll collar attached to the cell growth chamber, wherein the beveled pinion is movable in a direction parallel to a shaft rotation axis of the outer shaft member and the inner shaft member. In at least one embodiment the beveled pinion is biased in a longitudinally distal position by a means for biasing. Embodiments may further include a means for transferring torque located between the inner shaft member and the beveled pinion. In at least one embodiment the means for rolling comprises a beveled pinion that contacts a sloped surface of a roll collar attached to the cell growth chamber, wherein the beveled pinion contacts the sloped surface substantially along a contact line, and wherein the contact line is oriented at an oblique angle relative to the longitudinal axis of the cell growth chamber. In at least one embodiment the means for rolling and the means for pitching comprise independently controllable motors.

One or more embodiments are also directed at a method for rotating a cell growth chamber of a cell expansion system. Accordingly, a method of rotating a cell growth chamber of a cell expansion system around two different axes is provided, wherein a first of the two axes is a longitudinal axis of the cell growth chamber, and wherein a second of the two axes is an axis substantially perpendicular to the longitudinal axis of the cell growth chamber, the method comprising:

attaching a shaft fitting of a chamber coupling to an outer shaft member of a shaft assembly; and causing an inner shaft member located radially to the interior of the outer shaft member to rotate the cell growth chamber around the longitudinal axis of the cell growth chamber.

In at least one embodiment the method further comprises causing the outer shaft member to rotate, thereby rotating the longitudinal axis of the cell growth chamber. In at least one embodiment the method further comprises detaching the chamber coupling from the shaft assembly by releasing the shaft fitting and attaching a second chamber coupling to the shaft assembly.

As used herein, "at least one," "one or more," and "and/or" are open-ended expressions that are both conjunctive and disjunctive in operation. For example, each of the expressions "at least one of A, B and C," "at least one of A, B, or C," "one or more of A, B, and C," "one or more of A, B, or C" and "A, B, and/or C" means A alone, B alone, C alone, A and B together, A and C together, B and C together, or A, B and C together.

Various embodiments of the present inventions are set forth in the attached figures and in the Detailed Description as provided herein and as embodied by the claims. It should be understood, however, that this Summary does not contain all of the aspects and embodiments of the one or more present inventions, is not meant to be limiting or restrictive in any manner, and that the invention(s) as disclosed herein is/are and is understood by those of ordinary skill in the art to encompass obvious improvements and modifications thereto.

Additional advantages of the embodiments presented herein will become readily apparent from the following discussion, particularly when taken together with the accompanying drawings.

BRIEF DESCRIPTION OF THE DRAWINGS

FIGS. 19A-C are various views of a tube routing clip embodiment.

The drawings are not necessarily to scale.

DETAILED DESCRIPTION

The present disclosure is generally directed to a system for rotating a cell growth chamber of a cell expansion system. More particularly, as set forth below, at least one embodiment comprises a system for rotating a cell growth chamber about a first rotational axis and also about a second rotational axis.

Figure 1:
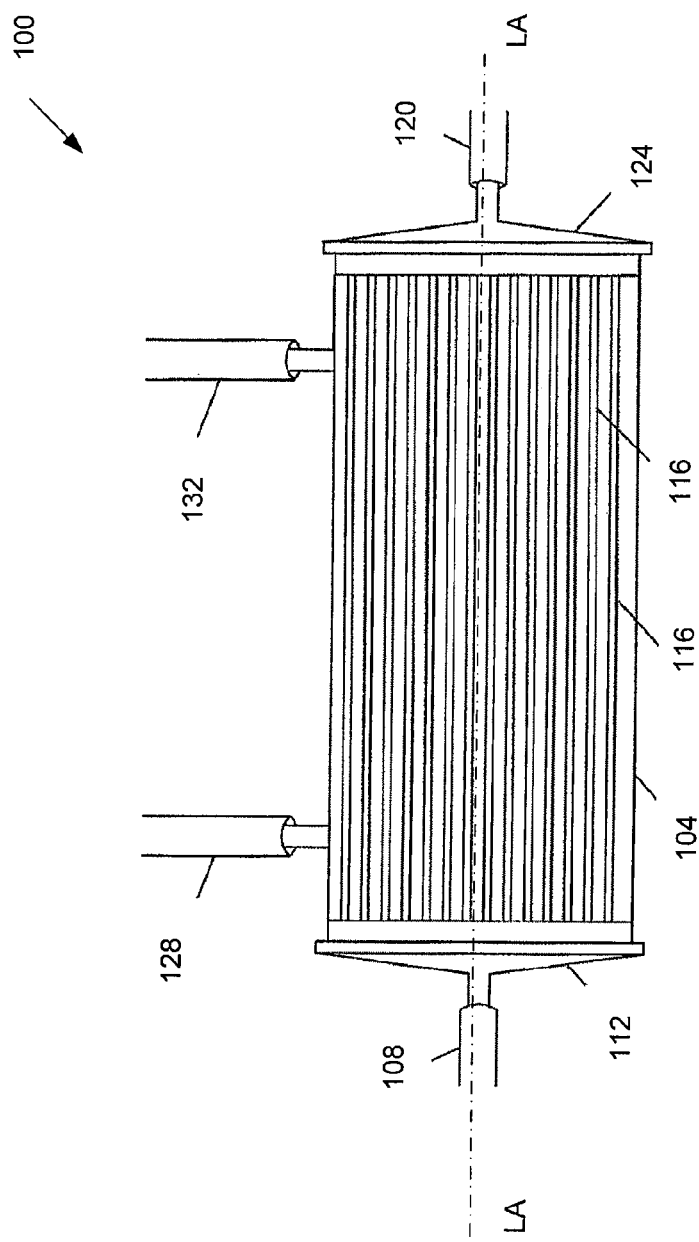
FIG. 1 is a front elevation view of an embodiment of a cell growth chamber.

With reference now to FIG. 1, an example of a cell growth chamber 100 is shown in front elevation view. Cell growth chamber 100 has a longitudinal axis LA-LA and includes cell growth chamber housing 104. In at least one embodiment, cell growth chamber housing 104 includes four openings or ports: IC inlet port 108, IC outlet port 120, EC inlet port 128, and EC outlet port 132.

Fluid in a first circulation path enters cell growth chamber 100 through IC inlet port 108 at a first longitudinal end 112 of the cell growth chamber 100, passes into and through the intracapillary side (referred to in various embodiments as the intracapillary ("IC") side or "IC space" of a hollow fiber membrane) of a plurality of hollow fibers 116, and out of cell growth chamber 100 through IC outlet port 120 located at a second longitudinal end 124 of the cell growth chamber 100. Fluid in a second circulation path flows in the cell growth chamber 100 through EC inlet port 128, comes in contact with the extracapillary side or outside (referred to as the "EC side" or "EC space" of the membrane) of the hollow fibers 116, and exits cell growth chamber 100 via EC outlet port 132. Fluid entering cell growth chamber via an EC inlet port 128 is in contact with the outside of the hollow fibers. Small molecules (e.g. water, oxygen, lactate, etc.) can diffuse through the hollow fibers from the interior of the hollow fiber to the EC space, or from the EC space to the IC space. Large molecular weight molecules such as growth factors are typically too large to pass through the hollow fibers, and remain in the IC space of the hollow fibers. The media may be replaced as needed. Media may also be circulated through an oxygenator to exchange gasses as needed. Cells can be contained within the first circulation path and/or second circulation path, and can be on either the IC side and/or EC side of the membrane.

Although cell growth chamber housing 104 is depicted as cylindrical in shape, it could have a variety of shapes, such as a rectangular cube. Cell growth chamber housing 104 can be made of any type of biocompatible polymeric material, including substantially transparent material that permits an observer to see one or more of the plurality of hollow fibers 116, as well as fluid residing within the cell growth chamber housing 104. Various other cell growth chamber housings may differ in shape and size.

Figure 2:
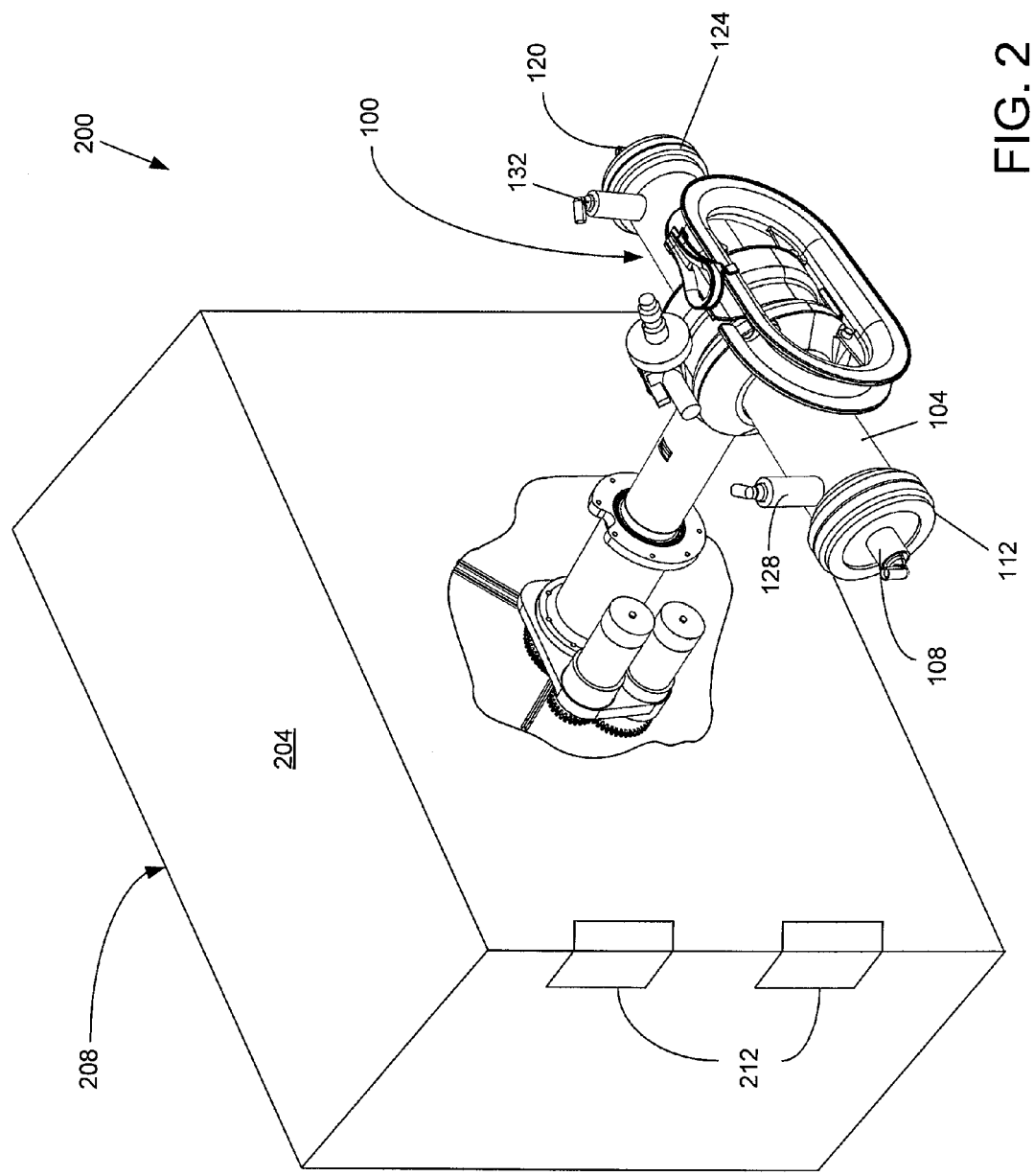
FIG. 2 is a perspective view of a portion of a cell expansion system, including a detachably attached cell growth chamber.

Referring now to FIG. 2, a portion of a CES 200 is shown in perspective view, and includes a back portion 204 of body 208 of the CES 200. For clarity, the front portion is not shown; however, the front portion is preferably attached to the back portion 204, such as by hinges 212, thereby allowing the front portion to comprise a door or hatch that can be opened to access the cell growth chamber 100 of the CES 200. The environment in the vicinity of the cell growth chamber 100 is temperature controlled to provide appropriate conditions for cell growth.

Figure 3:
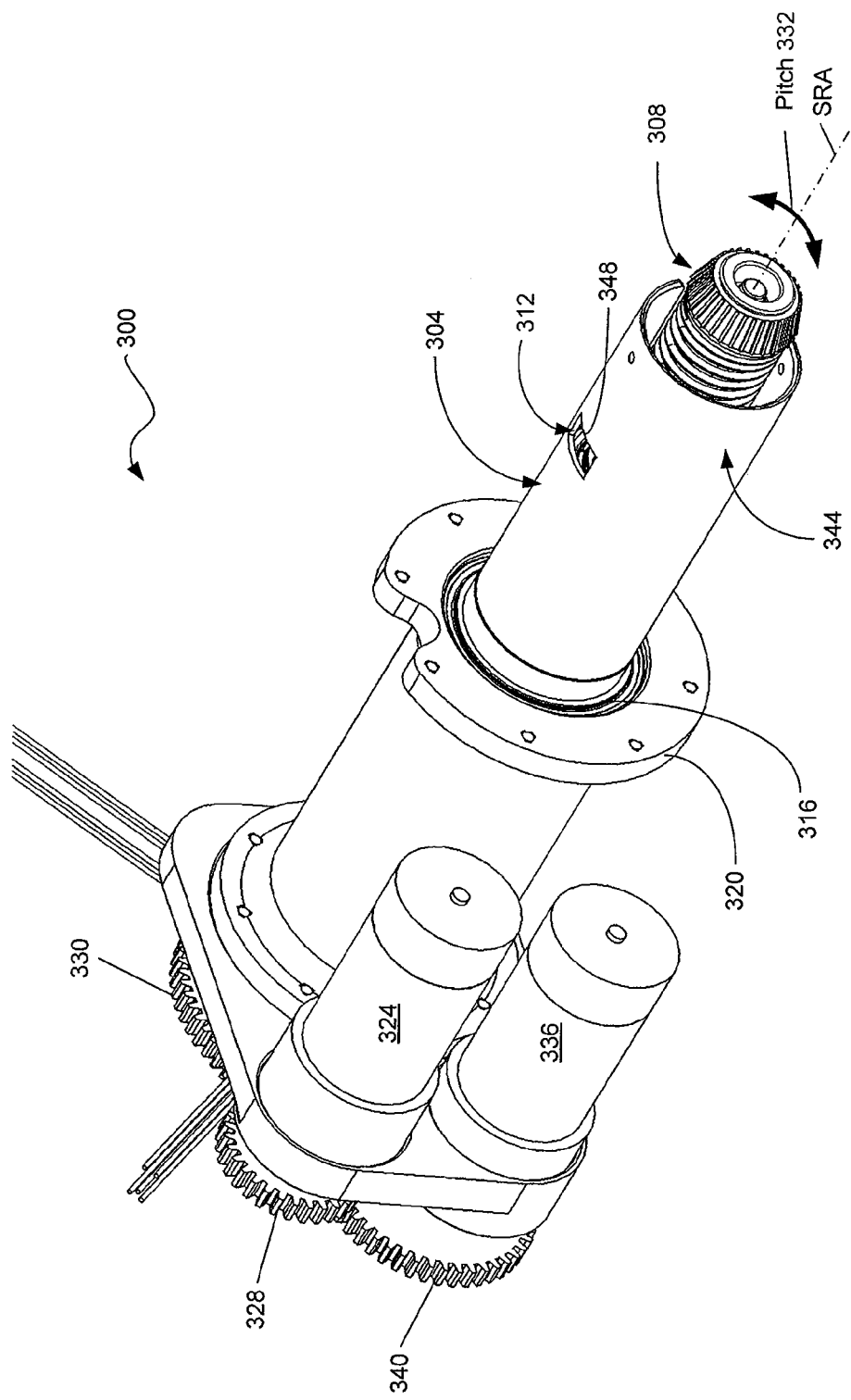
FIG. 3 is a perspective view of an embodiment of a shaft assembly of the cell expansion system.
Figure 4:
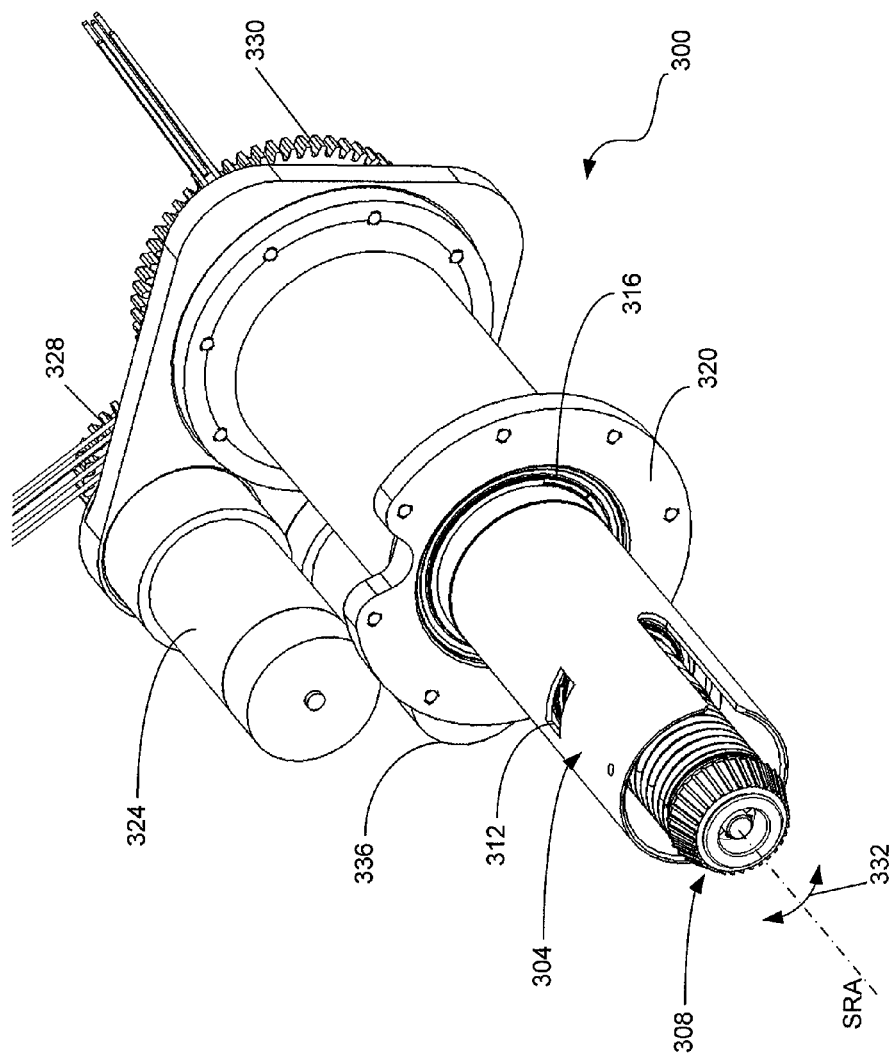
FIG. 4 is another perspective view of the shaft assembly depicted in FIG. 3.

With reference now to FIGS. 3 and 4, the shaft assembly 300 of the CES 200 is shown without the cell growth chamber. The shaft assembly 300 includes an outer shaft member 304 and an inner shaft member 308, wherein the inner shaft member 308 is coaxially aligned along shaft rotation axis SRA with the outer shaft member 304. In at least one embodiment, the outer shaft member 304 includes a pair of receptacles 312 (see FIG. 8) for receiving a latching element of the detachably attachable cell growth chamber (described below). The outer shaft member 304 is in contact with a bearing assembly 316 that couples the outer shaft member 304 to the housing flange 320 of the back portion 204 of body 208. A first motor 324 is selectively operable to rotate gear 328, which in turn rotates outer shaft gear 330 that rotates the outer shaft member 304, thereby rotating the cell growth chamber 100 in a first rotation orientation or pitch 332 about the shaft rotation axis SRA when the cell growth chamber 100 is attached to the shaft assembly 300. Second motor 336 is selectively operable to rotate gear 340, which in turn rotates the inner shaft member 308, thereby rotating the cell growth chamber 100 in a second rotation orientation or roll 600, as described below and shown in FIG. 6. Accordingly, in at least one embodiment, the outer shaft member 304 controls the pitch 332 of the cell growth chamber, and the inner shaft member 308 controls the roll 600 of the cell growth chamber 100.

Figure 5:
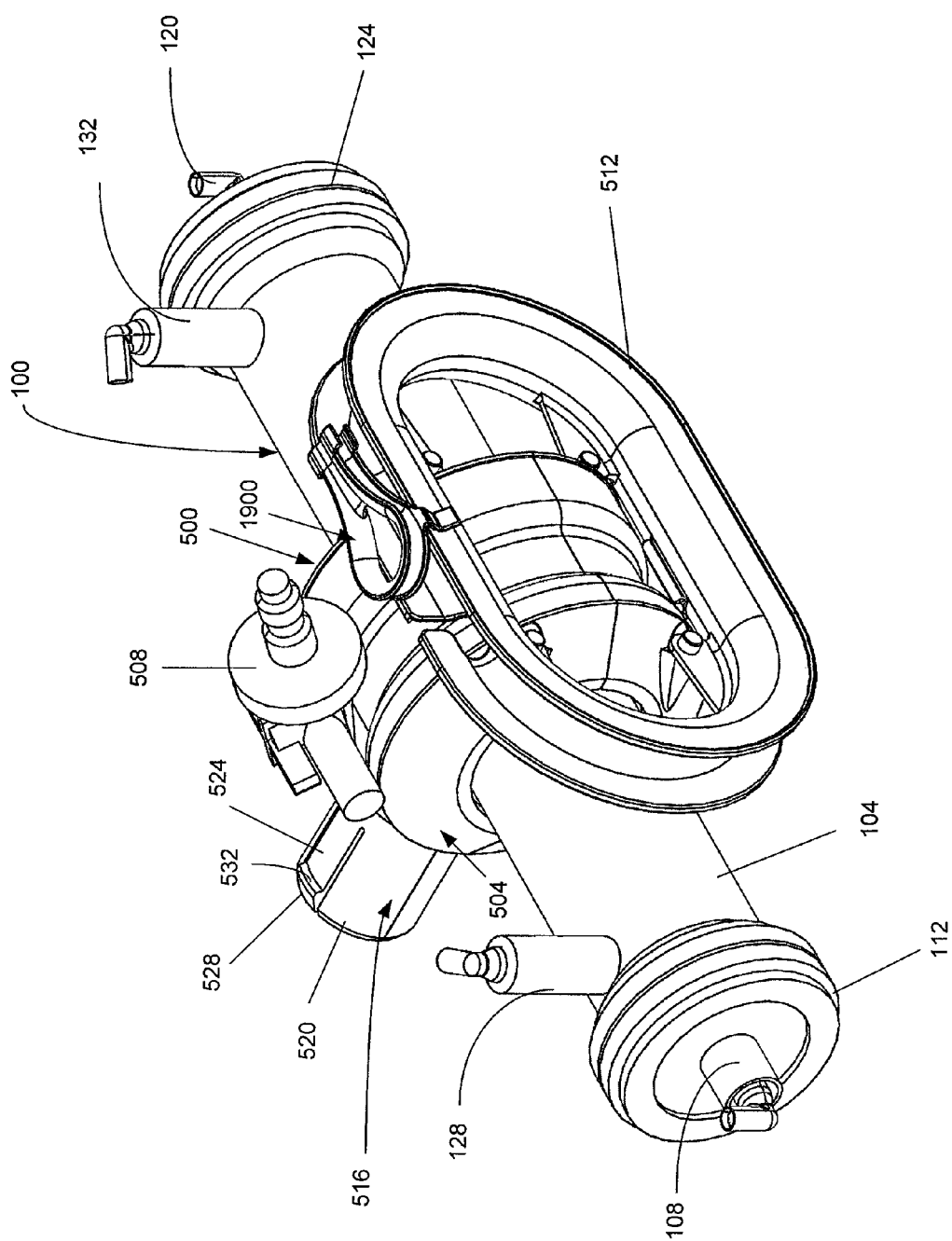
FIG. 5 is a perspective view of the chamber coupling and the cell growth chamber.

Referring now to FIG. 5, a perspective view of the cell growth chamber 100 is shown, wherein the cell growth chamber 100 is connected to chamber coupling 500. The chamber coupling 500 includes a chamber housing 504 that includes a roll collar 1100 (described below), wherein the roll collar 1100 is fixed to the cell growth chamber 100, and wherein the roll collar 1100 is rotatable within the chamber housing 504. In at least one embodiment, the chamber housing 504 comprises at least two pieces that are fastened together, such as by using a clamp, cable ties, bolts, screws and/or ultrasonically welding. More particularly, the roll collar 1100 is first fixedly attached to the exterior of the cell growth chamber 100, and then the chamber housing 504 is assembled over the roll collar 1100 and fastened together.

In accordance with at least one embodiment, a sample port 508 is connected to the exterior of the chamber housing 504 of the chamber coupling 500. The sample port 508 can be used to sample fluids within the tubing of the CES 200. In addition, tubing spool 512 may also be attached to the chamber housing 504. The tubing spool 512 is used to hold a length of tubing (not shown) that can be sampled using a sterile tubing welder during operation of the CES 200.

The position of the tubing spool 512 adjacent the cell growth chamber 100 allows the tubing to be subject to the same environmental conditions as those influencing the cell growth chamber 100. For example, the temperature of the tubing wound around the tubing spool 512 will be substantially the same as the temperature of the cell growth chamber. As a result, the fluid and cell conditions in the tubing spool 512 are substantially identical to those within the cell growth chamber 100. Therefore, analysis of samples of fluid and cells taken from the tubing wound around the tubing spool 512 allows operators of the CES 200 to understand the conditions residing with the cell growth chamber 100 itself.

Referring still to FIG. 5 as well as FIG. 3, in at least one embodiment the chamber coupling 500 includes a shaft fitting 516 for mating with the outer shaft member 304 of the shaft assembly 300. More particularly, the shaft fitting 516 includes a cylindrical male portion 520 for insertion in a distal end 344 of the outer shaft member 304. The cylindrical male portion 520 includes one or more spring members 524 having a beveled distal end 528 and shoulder 532. The beveled distal end 528 deflects upon insertion of the cylindrical male portion 520 into the distal end 344 of the outer shaft member 304. Once the shoulder 532 clears the front edge 348 of the receptacle 312 of the outer shaft member 304, the spring member 524 moves radially outward and causes the shoulder 532 to engage the front edge 348 of the receptacle 312 to releasably lock the chamber coupling 500 and the cell growth chamber 100 to the shaft assembly 300. As those skilled in the art will appreciate, the spring member 524 requires sufficient flexibility to allow the beveled distal end 528 to deflect inward as the cylindrical male portion 520 is inserted into the distal end of 344 of the outer shaft member 304, while also being sufficiently resilient to allow the beveled distal end 528 to spring back and enter the receptacle 312 of the outer shaft member 304 such that the shoulder 532 releasably locks the chamber coupling 500 to the outer shaft member 304. In addition, in operation, spring member 524 must also maintain the engagement of the chamber coupling 500 to the shaft assembly 300 as the cell growth chamber 100 is rotated and/or otherwise manipulated. Furthermore, once the cells have been harvested from the cell growth chamber 100, the spring members 524 must be capable of being manipulated by an operator of the CES 200 to deflect the spring members 524 radially inward until the shoulder 532 clears the front edge 348 of the receptacle 312 so that the cell growth chamber 100 and its chamber coupling 500 can be pulled out and removed from the shaft assembly 300.

Other embodiments may comprise one or more supplemental and/or alternative engaging mechanisms to connect the chamber coupling 500 to the outer shaft member 304. By way of example and not limitation, such supplemental and/or alternative engaging mechanisms may comprise a threaded coupling, one or more set screws, detents, screws, bolts, bayonet pins and/or other fasteners.

Figure 6:
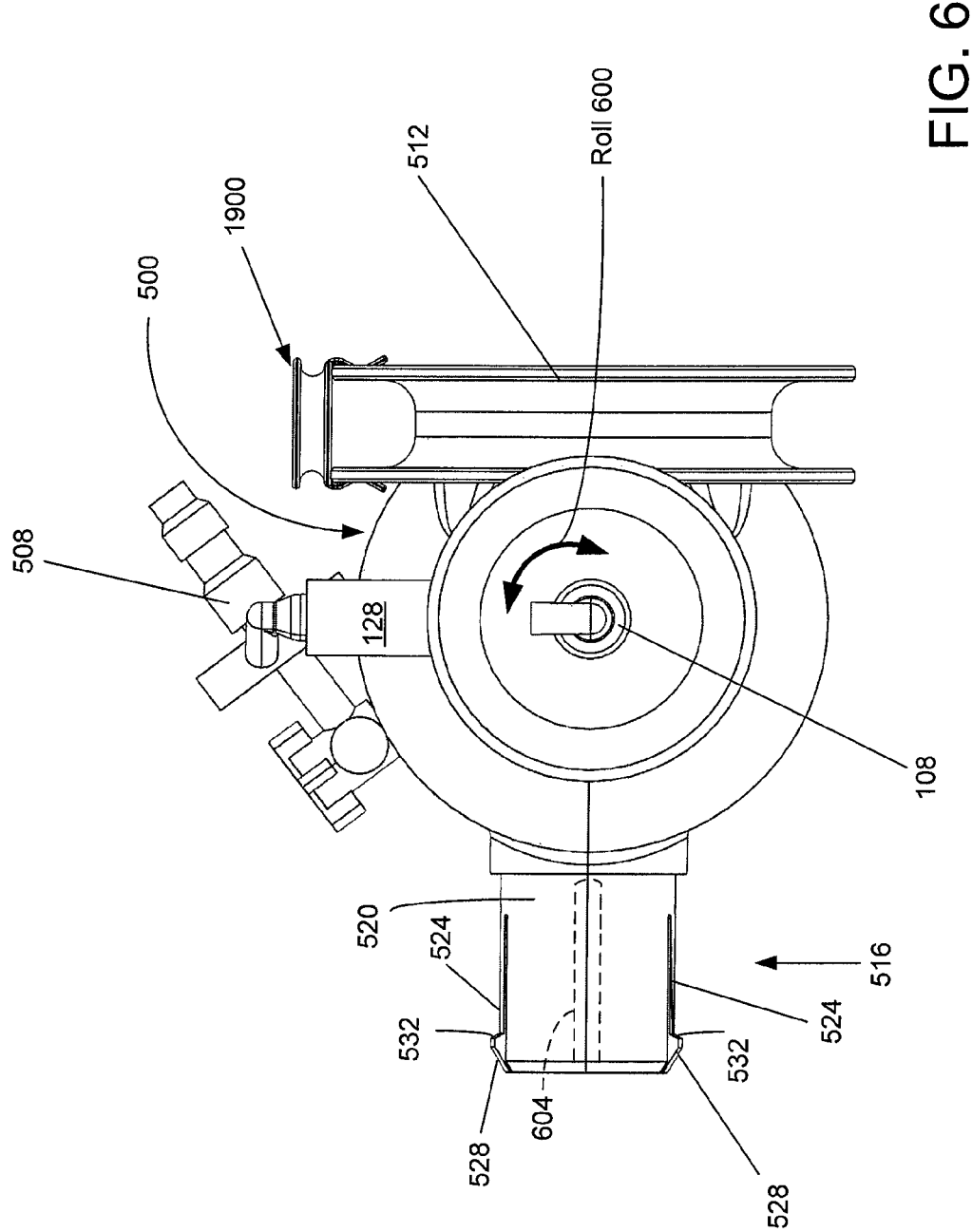
FIG. 6 is a side elevation view of the chamber coupling and the cell growth chamber.
Figure 7:
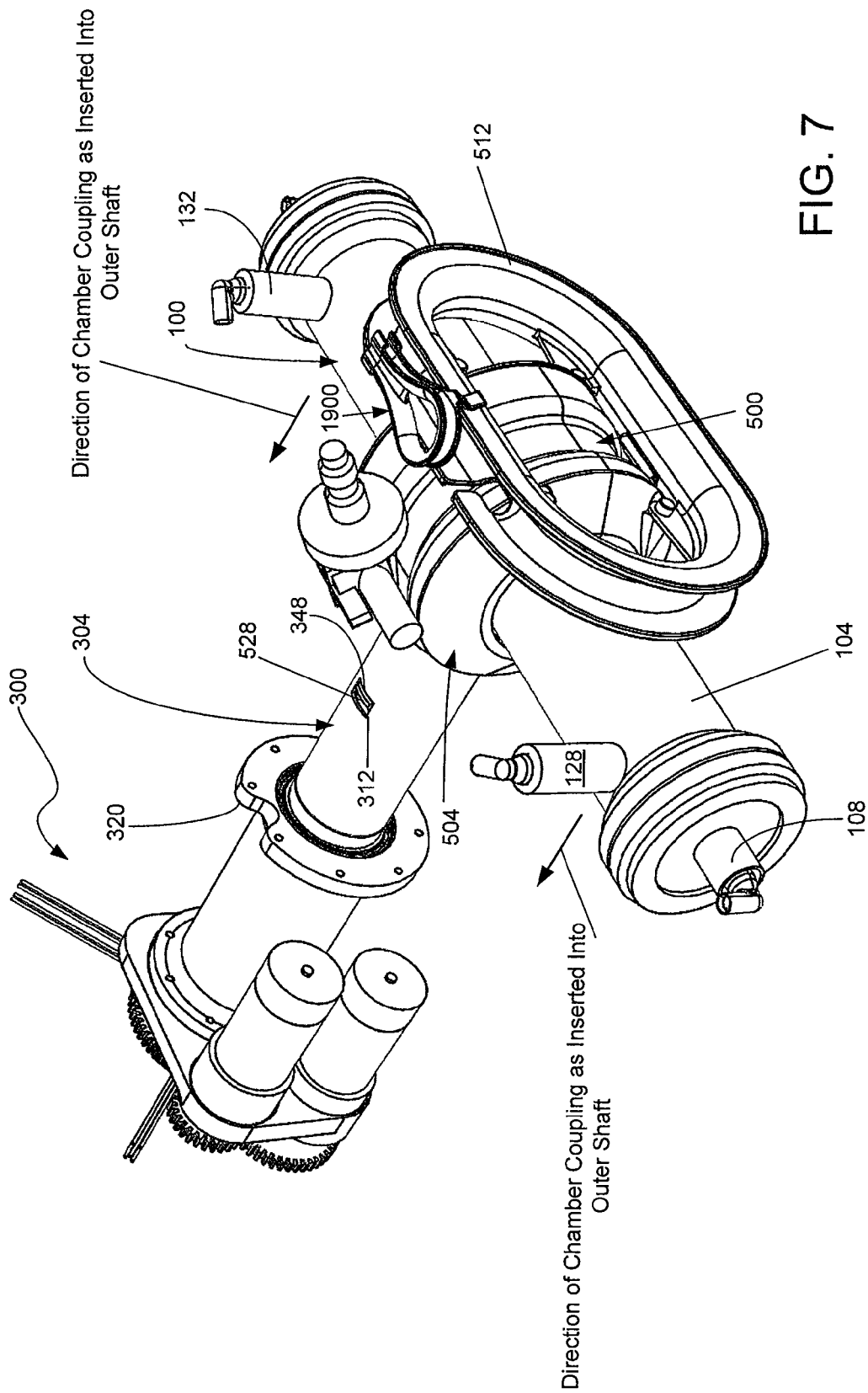
FIG. 7 is a perspective view of the shaft assembly connected to the chamber coupling that holds the cell growth chamber.
Figure 8:
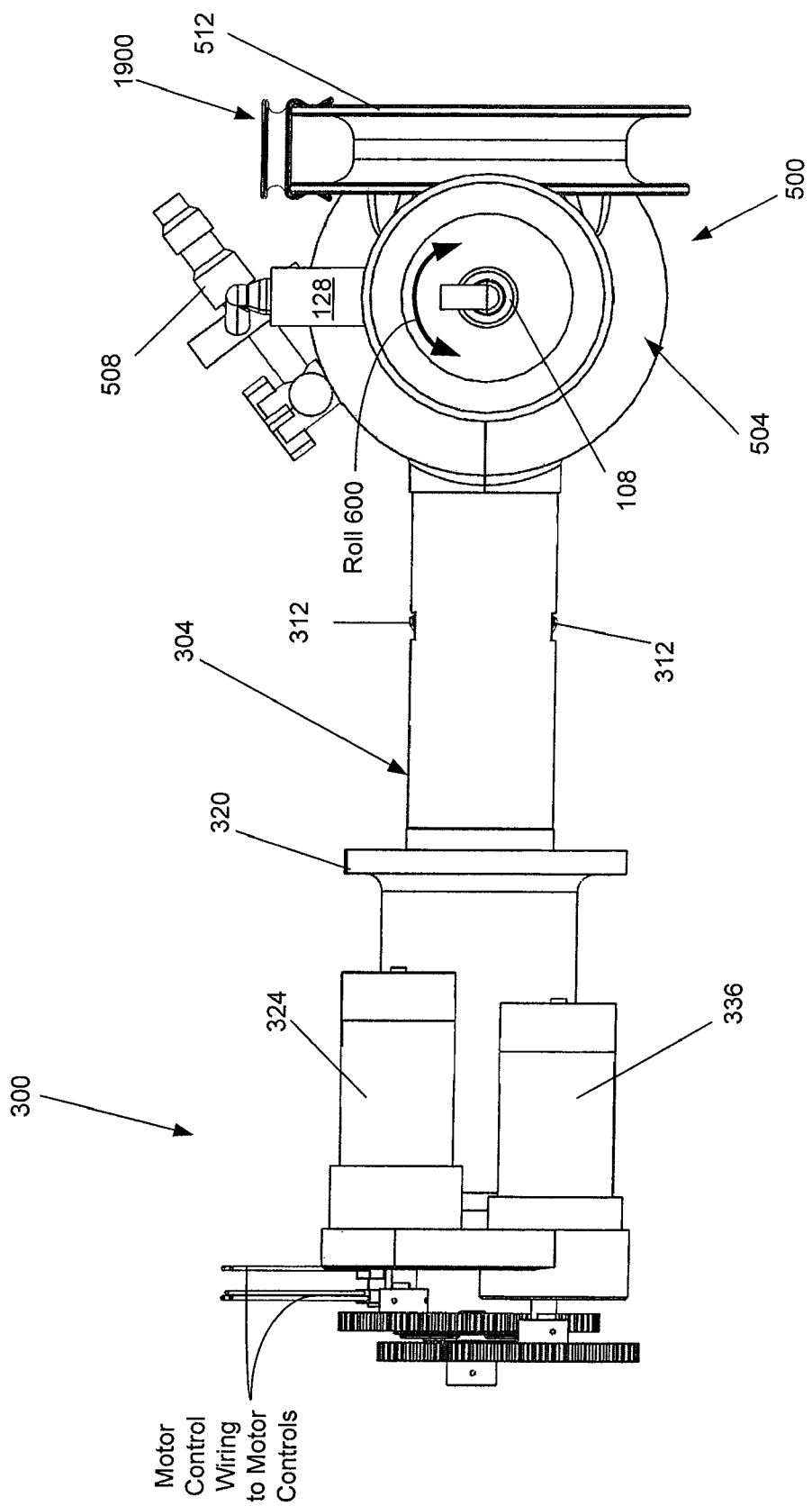
FIG. 8 is a side elevation view of the shaft assembly connected to the chamber coupling that holds the cell growth chamber.
Figure 9:
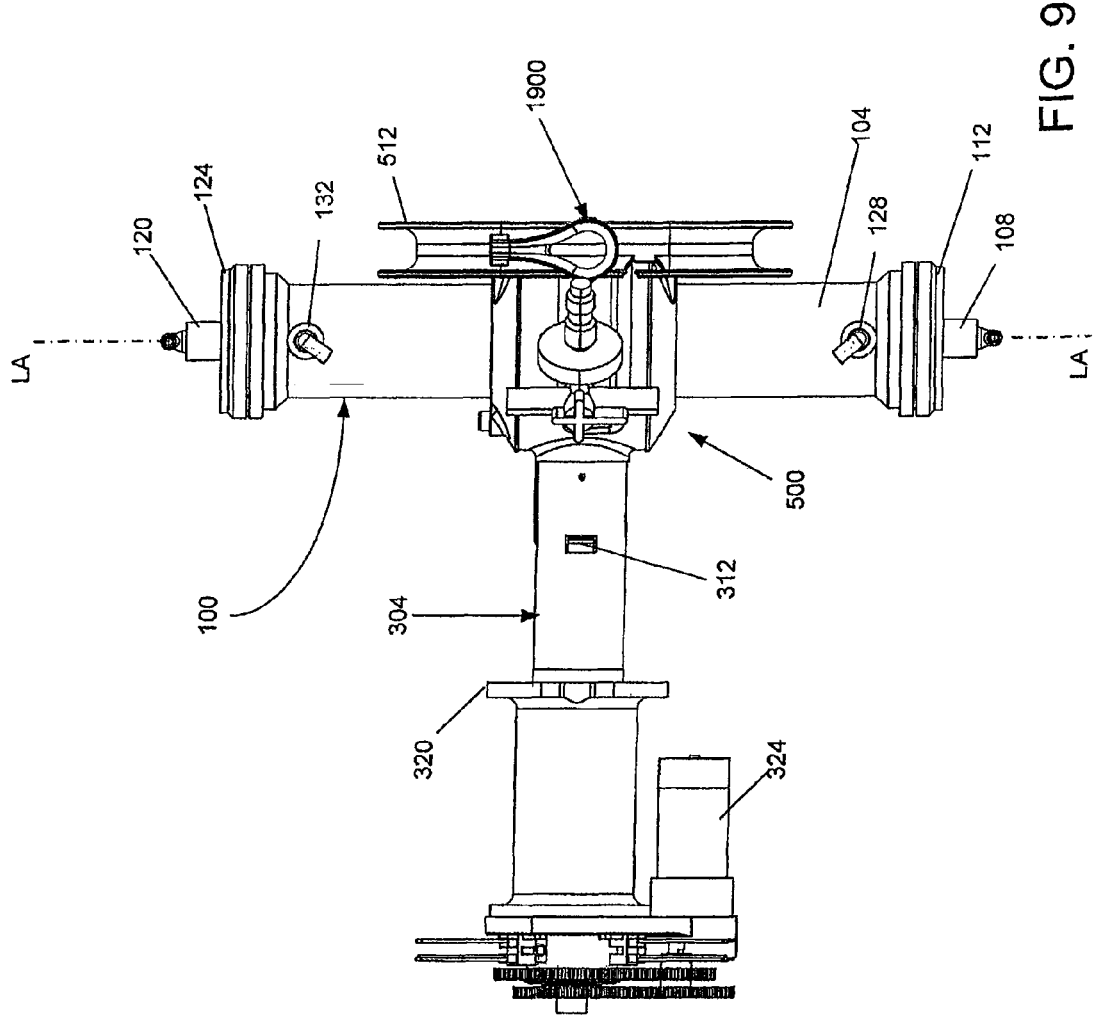
FIG. 9 is a top plan view of the shaft assembly connected to the chamber coupling that holds the cell growth chamber.

Referring now to FIG. 6, a side elevation view of the chamber coupling 500 is shown. As seen in FIG. 6, in at least one embodiment the cylindrical male portion 520 comprises a pair of spring members 524, wherein the spring members 524 are positioned on opposite sides of the cylindrical male portion 520. FIG. 6 also illustrates the position of the second rotation orientation or roll 600, which is rotation of the cell growth chamber 100 about its longitudinal axis LA-LA (which is into the page of FIG. 6). As used herein, "roll" is also defined as rotation of the cell growth chamber 100 such that the circumference of the cell growth chamber 100 is rotated about the longitudinal axis LA-LA, or an axis substantially parallel to the longitudinal axis LA-LA. Referring now to FIGS. 7-9, different views of the chamber coupling 500 are shown where the chamber coupling 500 is connected to shaft assembly 300. More particularly, the shaft fitting 516 of the cylindrical male portion 520 has been inserted into the distal end 344 of the outer shaft member 304 of the shaft assembly 300. The beveled distal ends 528 of the spring members 524 have been advanced in an axial direction of the outer shaft member 304, such that the shoulders 532 of the spring members 524 have engaged the front edge 348 of the receptacles 312.

Figure 10:
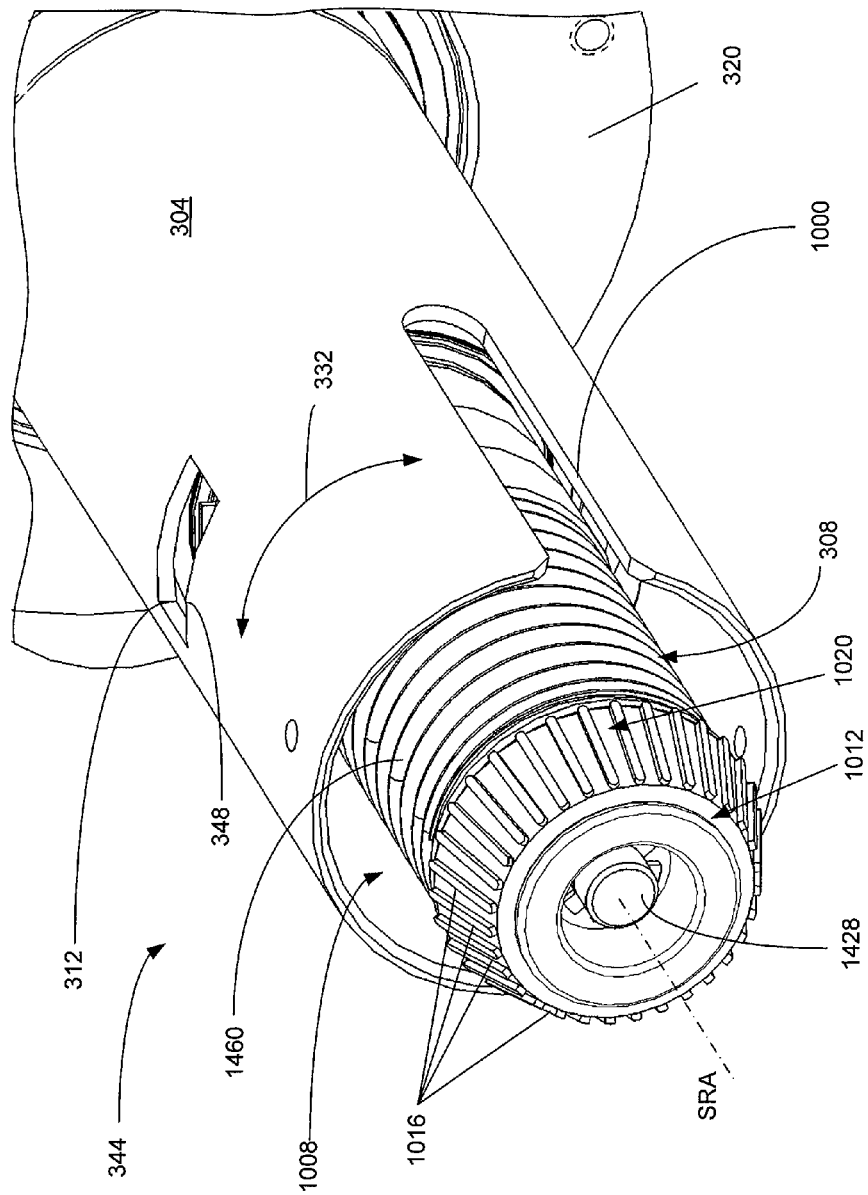
FIG. 10 is a detailed perspective view of the distal end of the outer shaft member and inner shaft member of the shaft assembly.

Referring now to FIG. 10, a detail view of the distal end of the shaft assembly 300 is shown. In at least one embodiment, the outer shaft member 304 may comprise a guide channel 1000 to serve as a guide for the insertion of the cylindrical male portion 520 of the chamber coupling 500. More particularly, guide channel 1000 is sized to receive an alignment guide or guide ridge 604 (shown as a dashed line in FIG. 6) positioned along an exterior lateral side of the cylindrical male portion 520. In use, an operator of the CES 200 aligns the guide ridge 604 to correspond to the guide channel 1000, and then inserts the shaft fitting 516 into the outer shaft member 304 until the beveled distal ends 528 of the spring members 524 are secured within the receptacles 312 of the outer shaft member 304.

With further reference to FIG. 10, the inner shaft member 308 can be seen positioned radially interior of the outer shaft member 304. In at least one embodiment the inner shaft member 308 is independently rotatable of the outer shaft member 304, such that either may be operated separately or operated at the same time. In general, the outer shaft member 304 rotates the cell growth chamber 100 in pitch mode by moving the cell growth chamber 100 either in a clockwise or counter clockwise manner, as per arrow 332, around the shaft rotation axis SRA.

Figure 11:
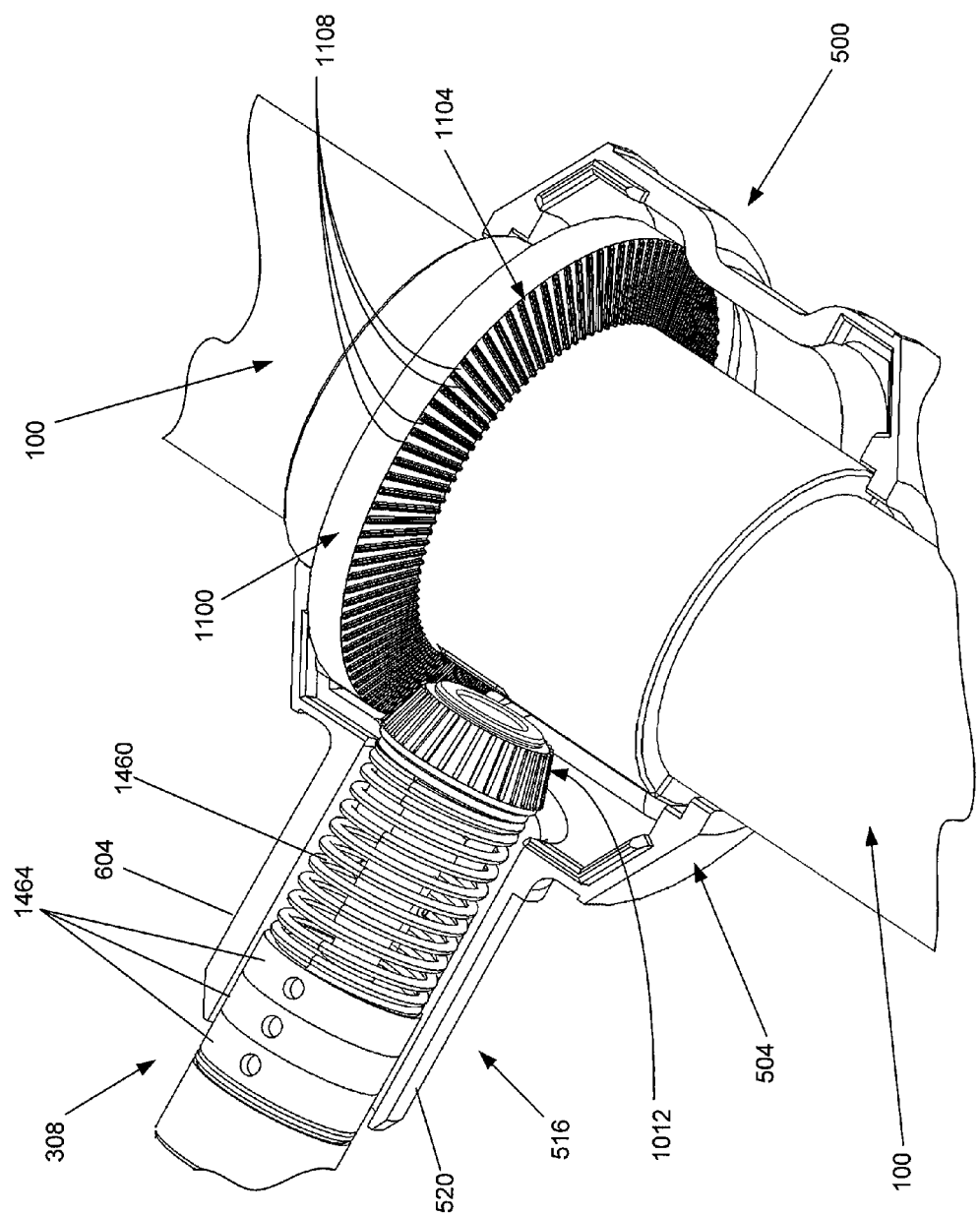
FIG. 11 is a cut-away perspective view of the chamber coupling when engaged by the distal end of the inner shaft member.
Figure 12:
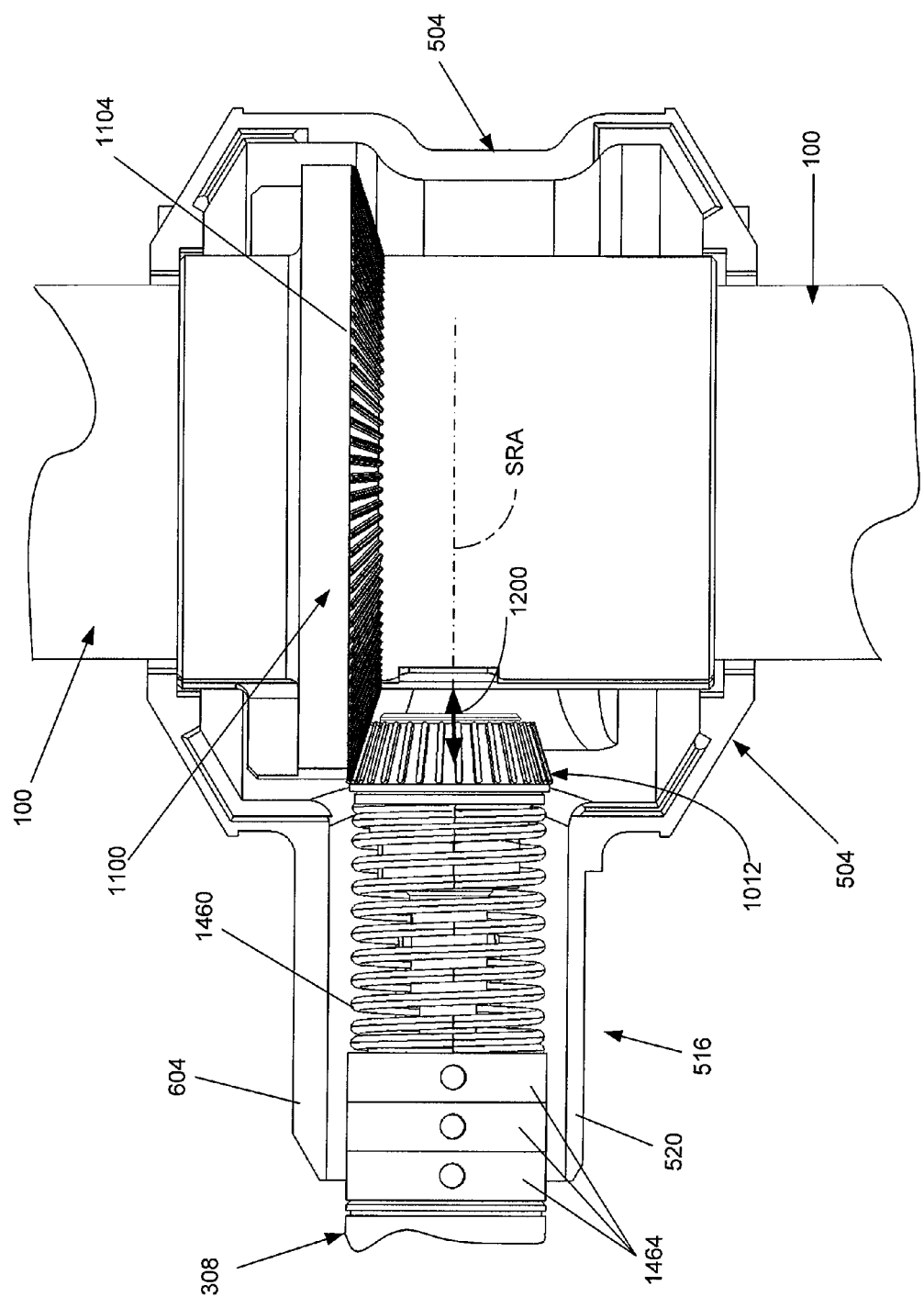
FIG. 12 is a cut-away plan view of the chamber coupling when engaged by the distal end of the inner shaft member.

Referring still to FIG. 10 as well as FIGS. 11 and 12, the distal end 1008 of the inner shaft member 308 includes structure for engaging a roll collar 1100 residing within the chamber housing 504 of the chamber coupling 500. In at least one embodiment, and as best seen in FIG. 11, the beveled surface 1020 of the beveled pinion 1012 engages the sloped surface 1104 of the roll collar 1100. More particularly, the inner shaft member 308 includes a beveled pinion 1012 residing at the very distal end of the inner shaft member 308, and the beveled pinion 1012 contacts the sloped surface 1104 of the roll collar 1100 such that when the inner shaft member 308 is rotated, the roll collar 1100 rotates, thereby causing the cell growth chamber 100 to rotate about its longitudinal axis LA-LA. As seen in FIG. 12, the beveled pinion 1012 can translate in the direction of the shaft rotation axis SRA (i.e., longitudinally along the axis of inner shaft member 308). This allows the beveled pinion 1012 to be moved axially as the chamber coupling 500 is attached to the outer shaft member 304. In so doing, the beveled surface 1020 of the beveled pinion 1012 is placed in contact with the sloped surface 1104 of the roll collar 1100 so that when the inner shaft member 308 is rotated, the rotation the inner shaft member 308 causes the roll collar 1100 to rotate the cell growth chamber 100 about its longitudinal axis LA-LA. The coil spring 1460 (discussed in detail below) acts as a biasing member to force the beveled surface 1020 to contact the sloped surface 1104 of the roll collar 1100. The beveled pinion 1012 may move axially in the direction of arrow 1200 back and forth when a chamber coupling 500 is attached and removed from the shaft assembly 300. Accordingly, the beveled pinion 1012 may move approximately 0.1 to 0.5 inches axially, and more preferably, approximately 0.2 to 0.4 inches axially, and more preferably yet, approximately 0.25 to 0.375 inches axially when the chamber coupling 500 is attached to the outer shaft member 304, thereby axially displacing the beveled pinion 1012 as the beveled surface 1020 seats and makes contact against the sloped surface 1104 of the roll collar 1100.

To achieve the rotation of the roll collar 1100, in at least one embodiment the beveled pinion 1012 includes a feature for frictionally engaging a sloped surface 1104 of the roll collar

1100. By way of example and not limitation, the beveled pinion 1012 may include a plurality of ribs 1016, such as thirty-two ribs per inch of the circumferential length of the beveled surface 1020 of the beveled pinion 1012. The sloped surface 1104 of the roll collar 1100 may also include a plurality of ribs 1108, wherein the ribs 1016 of the beveled surface 1020 of the beveled pinion 1012 engage the troughs between the ribs 1108 of the sloped surface 1104 of the roll collar 1100. Those skilled in the art will appreciate that the beveled surface 1020 may include alternative or different surficial features, such as texturing, gear teeth, and/or another type of feature for promoting frictional engagement between the beveled surface 1020 of the beveled pinion 1012 and the sloped surface 1104 of the roll collar 1100. In at least one embodiment, the beveled surface 1020 of the beveled pinion 1012 and/or the sloped surface 1104 of the roll collar 1100 comprise an elastomeric material.

Figure 13:
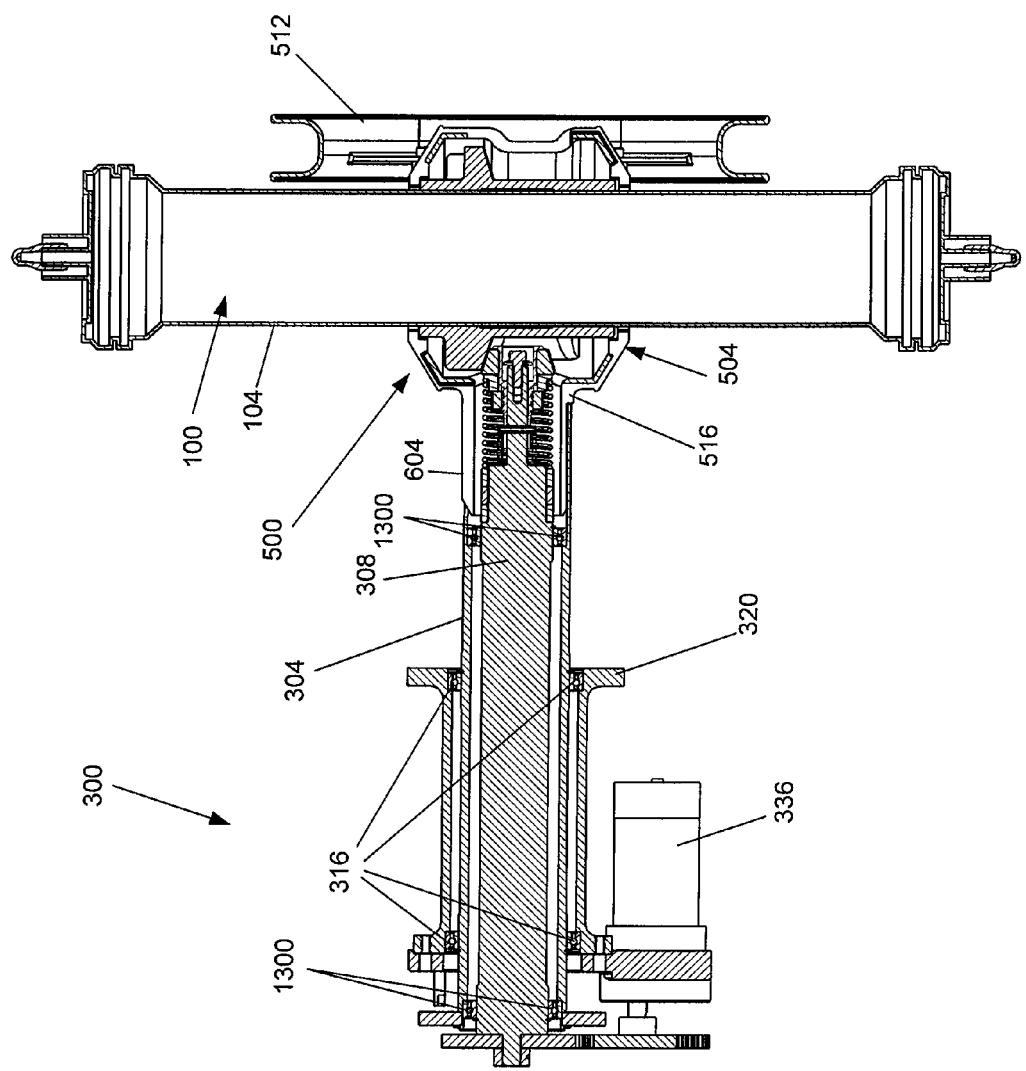
FIG. 13 is cross-sectional view of the chamber coupling when engaged by the shaft assembly.

Referring now to FIG. 13, a cross-sectional view of the shaft assembly 300 engaging the chamber coupling 500 with the cell growth chamber 100 is shown. FIG. 13 illustrates that there is a first plurality of bearings 316 to rotationally isolate the outer shaft member 304 from the housing flange 320, as well as a second radially interior plurality of bearings 1300 to rotationally isolate the outer shaft member 304 from the inner shaft member 308.

Figure 14:
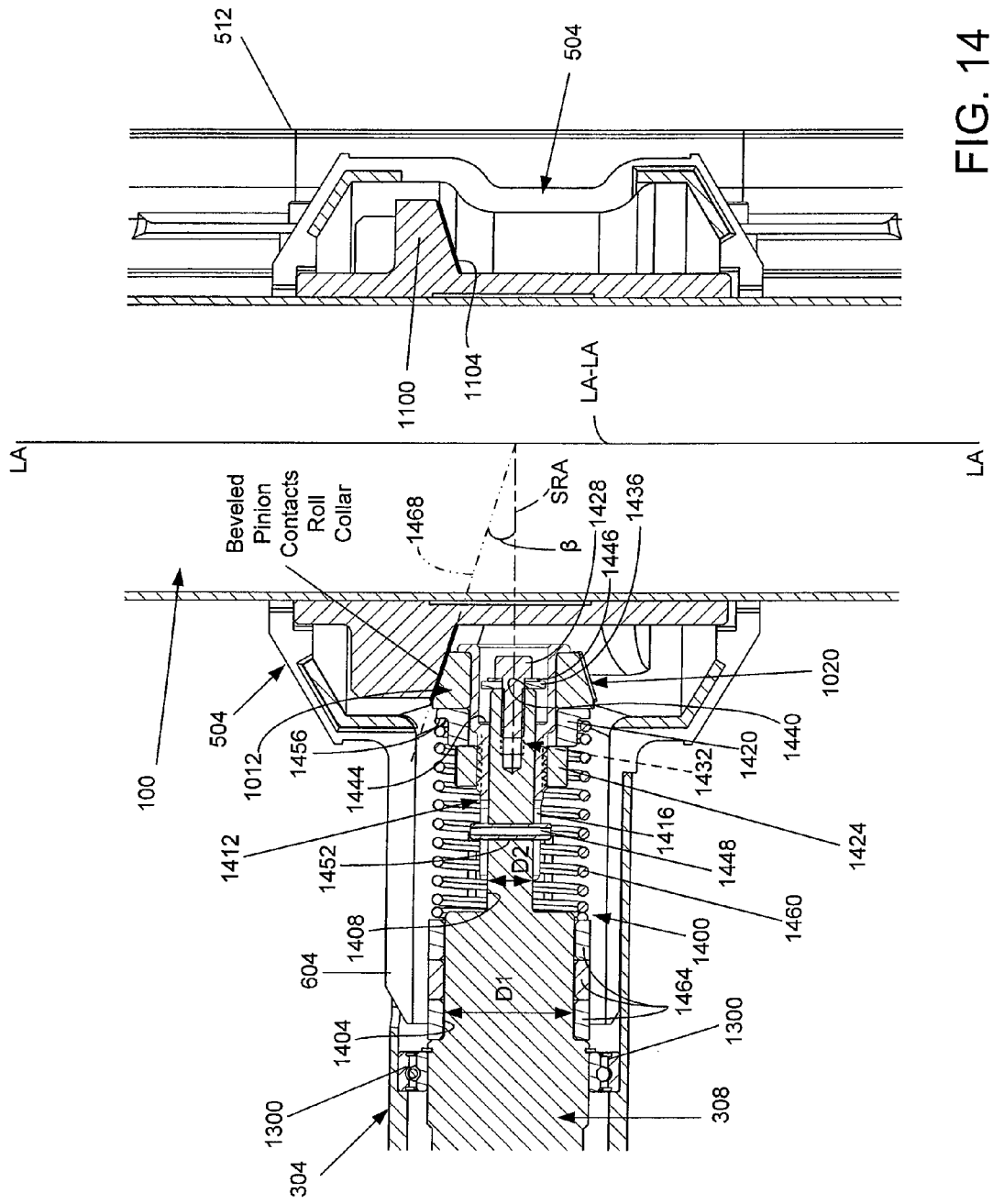
FIG. 14 is detailed cross-sectional view of the chamber coupling when engaged by the distal end of the inner and outer shaft members.
Figure 15:
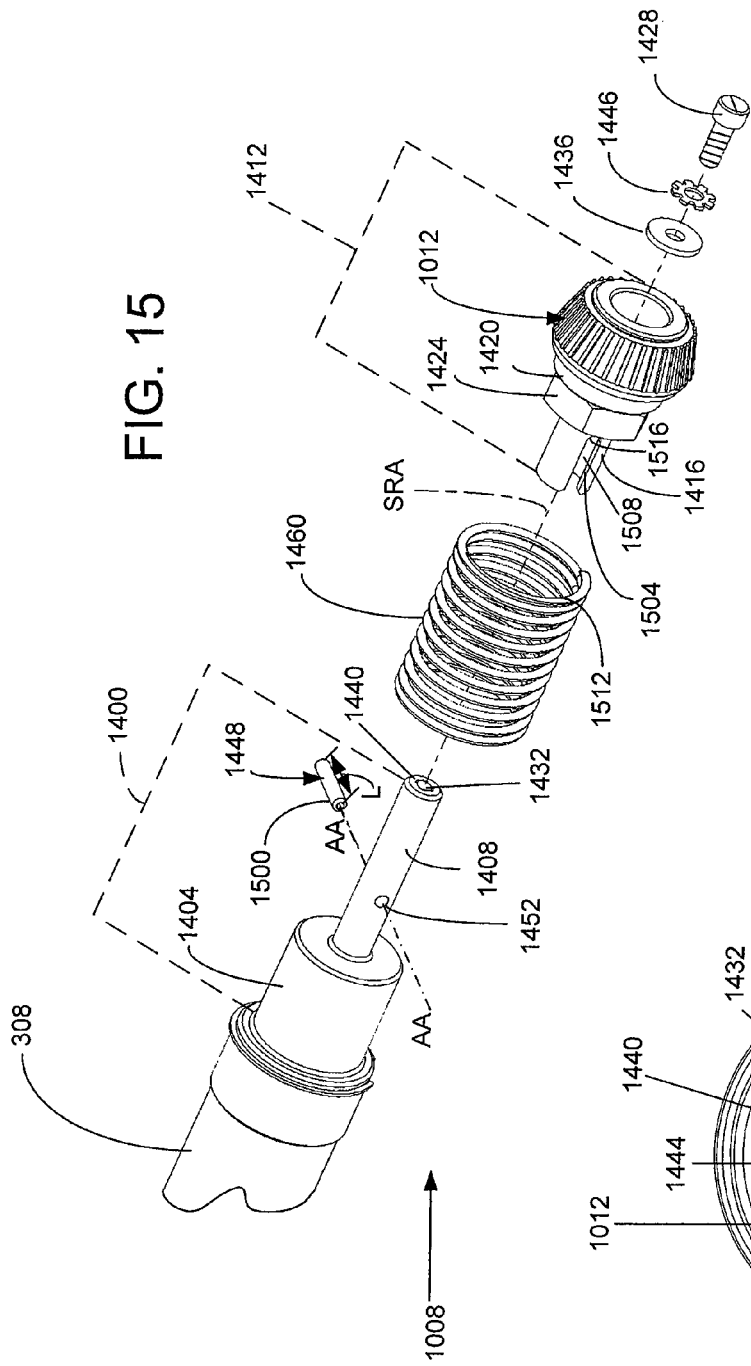
FIG. 15 is an exploded view of a portion of the inner shaft member.

With reference now to FIG. 14, a detailed cross-sectional view of the distal end of the shaft assembly 300 is illustrated engaging the chamber coupling 500. To further aid in illustrating the distal end of the shaft assembly 300, an exploded view of the distal end 1008 of the inner shaft member 308 is shown in FIG. 15. In at least one embodiment, the distal end 1008 of the inner shaft member 308 includes a receiving portion 1400 that further includes a first diameter portion 1404 and a second diameter portion 1408, wherein a diameter D1 of the of the first diameter portion 1404 is greater than a diameter D2 of the second diameter portion 1408. A beveled pinion fitting 1412 is detachably attached to the second diameter portion 1408. The beveled pinion fitting 1412 includes a slotted sleeve 1416 for slidably engaging the second diameter portion 1408 in a longitudinal orientation. The beveled pinion fitting 1412 includes the beveled pinion 1012 and the slotted sleeve 1416, that together may comprise a single integral piece. Alternatively, a backer ring 1420 and nut 1424 may be used to secure the beveled pinion 1012 to the slotted sleeve 1416.

Figure 16:
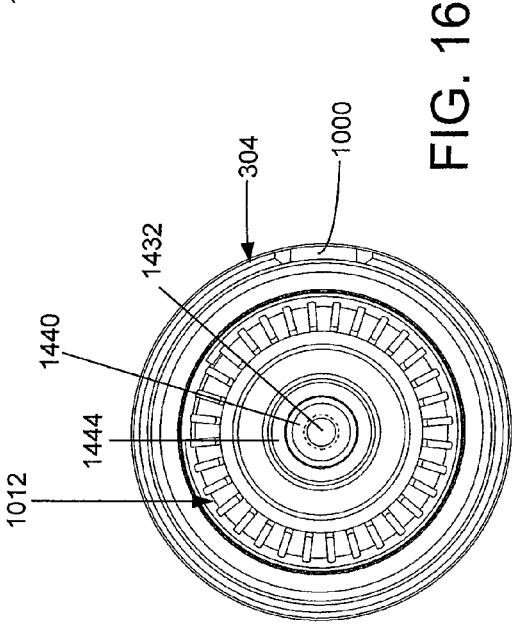
FIG. 16 is a front elevation view of the inner and outer shaft members, including the beveled pinion.

As noted above, the slotted sleeve 1416 slidably engages the second diameter portion 1408. The beveled pinion fitting 1412 is held in slidable engagement with the second diameter portion 1408 by a fastener, such as a bolt or screw 1428, that threads into aperture 1432. A flat washer 1436 contacts the distal face 1440 of the second diameter portion 1408. In addition, the flat washer 1436 serves to limit the longitudinal distal movement of the beveled pinion fitting 1412, and thus, the beveled pinion 1012, by blocking the longitudinal distal movement of the inner flange 1444 of the beveled pinion fitting 1412. The inner flange 1444 of the beveled pinion fitting 1412 can best be seen in FIGS. 14 and 16. A lock washer or star washer 1446 may be used between the flat washer 1436 and the screw 1428 to prevent the screw 1428 from backing out of the aperture 1432.

Referring now to FIGS. 14 and 15, a pin 1448 serves to transfer the torque from the inner shaft member 308 to the beveled pinion fitting 1412. More particularly, the pin 1448 resides within and extends radially beyond an aperture 1452, wherein an aperture axis AA-AA of the aperture 1452 is situated substantially perpendicular to the shaft rotational axis SRA. Accordingly, the pin has a length L, where L is greater than the diameter D2 of the second diameter portion 1408. When the inner shaft member 308 is rotated, a circumferential surface 1500 of the pin 1448 contacts a slot surface 1504 of a slot 1508 located in the slotted sleeve 1416 of the beveled pinion fitting 1412. In so doing, when the inner shaft member 308 is rotated, the pin 1448 transfers the torque to the slotted sleeve 1416, thereby causing the beveled pinion 1012 to rotate about its axis. The beveled pinion fitting 1412 is able to move in a proximal longitudinal direction along the second diameter portion 1408 because the ends of the pin 1448 reside within slot 1508.

To maintain the beveled pinion 1012 in contact with the roll collar 1100 of the chamber coupling 500, a back shoulder 1456 of the backer ring 1420 engages a distal end 1512 of a biasing member, such as coil spring 1460. Of course, if the backer ring 1420, nut 1424 and beveled pinion 1012 are an integral piece collectively with the slotted sleeve 1416, then the beveled pinion 1012 may include a back shoulder or similar structure for engaging the distal end 1512 of the coil spring 1460. As best seen in FIG. 14, one or more spacer rings 1464 may be used between the proximal end of the coil spring 1460 and the body of the inner shaft member 308 to adjust the force of the coil spring 1460 acting on the beveled pinion 1012. The coil spring 1460 serves to maintain the beveled pinion fitting 1412, and thus, the beveled pinion 1012, in a biased distal position so that the beveled pinion 1012 engages the roll collar 1100 to rotate the cell growth chamber 100 about its longitudinal axis LA-LA.

The longitudinal extent of movement of the beveled pinion fitting 1412 in the distal direction is limited by the inner flange 1444 of the beveled pinion fitting 1412 contacting the flat washer 1436. The longitudinal extent of movement of the beveled pinion fitting 1412 in the proximal direction is limited by the pin 1448 contacting a distal end 1516 of the slot 1508 residing within the slotted sleeve 1416.

Referring still to FIG. 14, the beveled surface 1020 of the beveled pinion 1012 contacts the sloped surface 1104 of the roll collar 1100 along contact line 1468. The orientation of the contact line 1468 intercepts the longitudinal axis LA-LA of the cell growth chamber 100 at an oblique angle. The bevel angle 13, defined as the angle formed between the shaft rotation axis SRA and the contact line 1468, is the inverse tangent of the ratio of the beveled pinion 1012 and the roll collar 1100 diameters, the diameters being measured at some point on the contact line 1468.

Figure 17A:
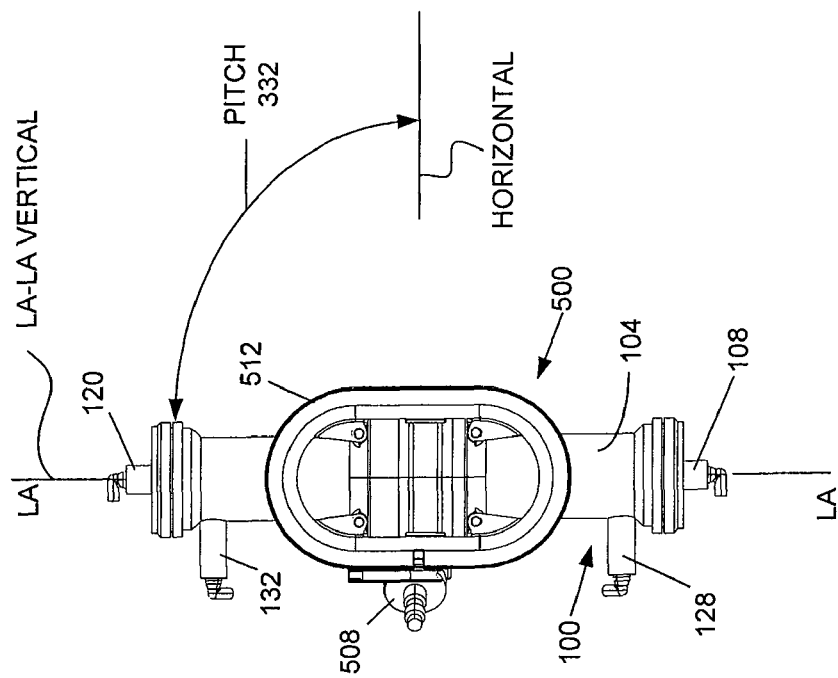
FIGS. 17A and 17B are front elevation views of the cell growth chamber and chamber coupling when rotated in pitch mode.
Figure 17B:
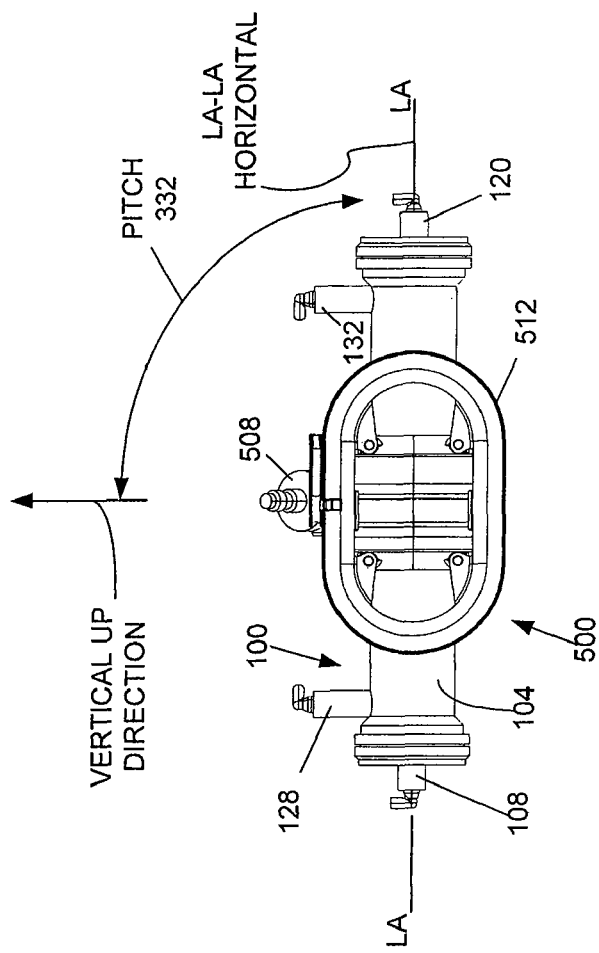

With reference now to FIGS. 17A and 17B, an example of rotating the cell growth chamber in the pitch mode is illustrated. In FIG. 17A, the longitudinal axis LA-LA is substantially horizontal, and in FIG. 17B, the longitudinal axis LA-LA is substantially vertical. It is to be understood that the pitch 332 of the cell growth chamber 100 can be selectively controlled such that the longitudinal axis LA-LA is rotated at any angle. That is, the longitudinal axis LA-LA of the cell growth chamber 100 can be rotated such that it is oriented at any angle θ to 360 degrees. For example, the longitudinal axis LA-LA can be oriented 45 degrees clockwise of vertical, or 60 degrees counter-clockwise of vertical. At a minimum, rotation of the cell growth chamber 100 in pitch mode assists in directing air or gas bubbles toward one or both of the IC outlet port 120 or EC outlet port 132 as the cell growth chamber 100 is being filled with a priming fluid in preparation for loading cells in the cell expansion system 200.

Figure 18:
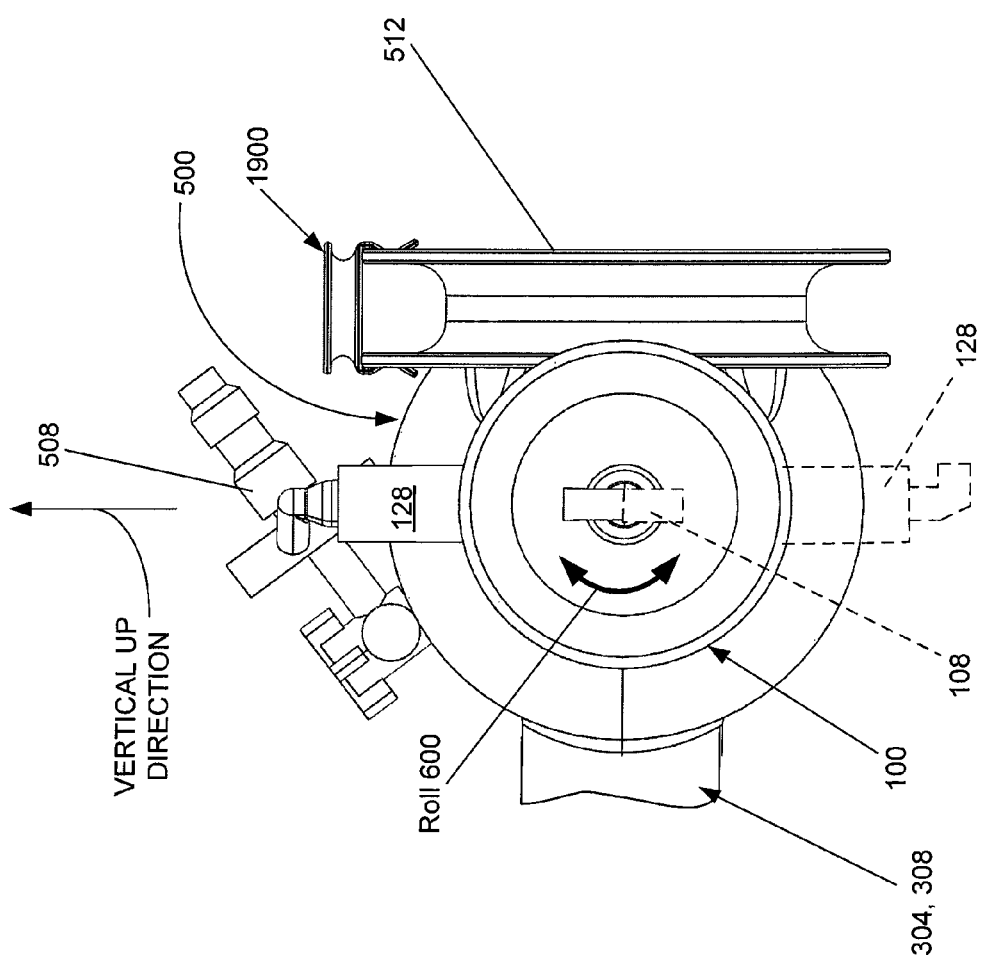
FIG. 18 is a side elevation view of the cell growth chamber and chamber coupling when rotated in roll mode, wherein dashed lines indicate a second orientation of the IC and EC inlet ports.

With reference now to FIG. 18, an example of rotating the cell growth chamber in the roll mode is illustrated. In FIG. 18, a side elevation view of the cell growth chamber 100 is shown, wherein in a first roll position (shown with solid lines), the EC inlet port 128 is oriented vertically upwards. In a second roll position (shown with dashed lines), the EC inlet port 128 is oriented downwards. It is to be understood that the roll 600 of the cell growth chamber 100 can be selectively controlled such that the cell growth chamber 100 can be rotated at any angle around its longitudinal axis. Periodic rotation of the cell growth chamber 100 assists in preventing colonies of cells from settling during the cell expansion process.

As those skilled in the art will appreciate, roll can be achieved by rotating the cell growth chamber around its longitudinal axis. Alternatively, roll may be achieved differently, such as by rotating a hinged arm that swings the cell growth chamber 100 from a first vertical upward position to a second vertical downward position (or any angle in between such positions). For such a configuration, the cell growth chamber rotates about an axis substantially parallel to the longitudinal axis of the cell growth chamber. The arm could then be tilted left or right to pitch the cell growth chamber. Thus, alternative ways of achieving pitch and roll are possible and are encompassed by the present disclosure.

In a separate embodiment, various views of a tube routing clip 1900 are shown in FIGS. 19A-C. The tube routing clip 1900 is used to provide a detachably attachable device with a sufficient radius of curvature for bending the tubing associated with the CES 200 without causing the tubing damage. More particularly, while the tubing spool 512 provides a length of tubing that can be sampled using a sterile tubing welder during operation of the CES 200, once the tubing has been cut and welded, the welds of the tubing are prone to kinking if bent in a relatively small radius. Accordingly, the tube routing clip 1900 allows the tubing to be turned in a 180 degree direction without causing the welds in the tubing to kink.

Referring still to FIGS. 19A-C, the tube routing clip 1900 includes a substantially teardrop-shaped body 1904. The perimeter of the body 1904 includes a routing channel 1908 for receiving the tubing T (shown in FIG. 19B only). The rear portion 1912 of the body 1904 includes a pair of C-shaped tubing receptacles 1916 that are sized for receiving and holding the tubing once the tubing is pushed into the pair of C-shaped tubing receptacles 1916. The front portion 1920 of the body 1904 includes a pair of spring clips 1924 for engaging the tubing spool 512. FIG. 5 illustrates the tube routing clip 1900 attached to the perimeter of the tubing spool 512.

In use, an operator of the CES 200 may periodically be tasked with obtaining a sample of the cells being grown in the cell growth chamber 100. The operator can remove a fluid-filled section of the tubing from the tubing spool 512 by using a sterile tubing welder. The length of the tubing remaining on the tubing spool 512 then includes a weld. The operator can place the tubing T with the weld W along the routing channel 1908 without causing a kink, wrinkle or blockage in the tubing. The spring clips 1924 allow the tube routing clip 1900 to be detached and reattached as may be needed to access the tubing held on the tubing spool 512, and to facilitate ease of manipulation of the tubing so that the weld W can be properly positioned along the routing channel 1908 prior to reattaching the routing clip 1900 to the tubing spool 512.

Various components may be referred to herein as "operably associated." As used herein, "operably associated" refers to components that are linked together in operable fashion, and encompasses embodiments in which components are linked directly, as well as embodiments in which additional components are placed between the two linked components.

The one or more present inventions may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The one or more present inventions, in various embodiments, include components, methods, processes, systems and/or apparatus substantially as depicted and described herein, including various embodiments, subcombinations, and subsets thereof. Those of skill in the art will understand how to make and use the present invention after understanding the present disclosure.

The one or more present inventions, in various embodiments, include providing devices and processes in the absence of items not depicted and/or described herein or in various embodiments hereof, including in the absence of such items as may have been used in previous devices or processes (e.g., for improving performance, achieving ease and/or reducing cost of implementation).

The foregoing discussion of the one or more present inventions has been presented for purposes of illustration and description. The foregoing is not intended to limit the one or more present inventions to the form or forms disclosed herein. In the foregoing Detailed Description for example, various features of the one or more present inventions are grouped together in one or more embodiments for the purpose of streamlining the disclosure. This method of disclosure is not to be interpreted as reflecting an intention that the claimed invention requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the one or more present inventions.

Moreover, though the description of the one or more present inventions has included description of one or more embodiments and certain variations and modifications, other variations and modifications are within the scope of the invention (e.g., as may be within the skill and knowledge of those in the art, after understanding the present disclosure). It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. An apparatus for rotating a cell growth chamber of a cell expansion system, the cell growth chamber including a longitudinal axis, the apparatus comprising:
    a shaft assembly including:
        an outer shaft member;
        an inner shaft member wherein at least a portion of the inner shaft member is located radially to an interior of the outer shaft member, wherein the outer shaft member and the inner shaft member are substantially coaxial and share a shaft rotation axis, the inner shaft member including a beveled pinion at a distal end of the inner shaft member, wherein the beveled pinion is translatable longitudinally along the shaft rotation axis, the beveled pinion including a beveled surface;
        a first motor for rotating the outer shaft member; and
        a second motor for rotating the inner shaft member;
    a chamber coupling connected to the cell growth chamber, the chamber coupling including a shaft fitting for detachably engaging the outer shaft member, the chamber coupling including a roll collar located around at least a portion of the cell growth chamber, the roll collar including a sloped surface for engaging the beveled pinion;

wherein when the first motor rotates the outer shaft member the cell growth chamber rotates around the shaft rotation axis, and wherein when the second motor rotates the inner shaft member the cell growth chamber rotates around the longitudinal axis of the cell growth chamber.

2. The apparatus of claim 1, wherein the beveled pinion comprises a substantially frusto-conical-shaped exterior including a surface for frictionally contacting the sloped surface of the roll collar.

3. The apparatus of claim 1, wherein the beveled pinion contacts the sloped surface along a contact line, the contact line oriented at an oblique angle relative to the longitudinal axis of the cell growth chamber.

4. The apparatus of claim 1, wherein the beveled pinion contacts the sloped surface along a contact line, and wherein a bevel angle β between the contact line and the shaft rotation axis is substantially an inverse tangent value of a ratio of a beveled pinion diameter to a roll collar diameter.

5. The apparatus of claim 1, wherein the inner shaft member includes a beveled pinion fitting, the beveled pinion fitting including a slotted sleeve that slidably engages a portion of the inner shaft member.

6. The apparatus of claim 5, wherein a pin transfers torque between the inner shaft member and the beveled pinion fitting.

7. The apparatus of claim 5, further comprising a biasing member for maintaining the beveled pinion in a distally biased position.

8. The apparatus of claim 1, wherein at least one of the shaft fitting and the outer shaft member comprise an alignment guide for properly orienting the chamber coupling for attachment to the outer shaft member.

9. The apparatus of claim 1, wherein the shaft fitting comprises at least one spring member having a beveled distal end and a shoulder, wherein the beveled distal end deflects upon insertion into the outer shaft member, and wherein once the shoulder clears a front edge of a receptacle of the outer shaft member, the at least one spring member moves radially outward and causes the shoulder to engage the front edge of the receptacle to detachably engage the chamber coupling and the cell growth chamber to the shaft assembly.

10. The apparatus of claim 1, wherein a tubing spool is connected to the chamber coupling, and wherein a tube routing clip is detachably attached to the tubing spool, the tube routing clip including a substantially teardrop-shaped tube routing channel for holding a section of tubing.

\* \* \* \* \*